(12) United States Patent
Stroobant

(10) Patent No.: US 7,208,268 B2
(45) Date of Patent: Apr. 24, 2007

(54) DIFFERENTIAL PHAGE CAPTURE PROTEOMICS

(76) Inventor: Paul Stroobant, 30 Morningside Ave., Natick, MA (US) 01760

( * ) Notice: Subject to any disclaimer, the term of this patent is extended or adjusted under 35 U.S.C. 154(b) by 332 days.

(21) Appl. No.: 10/022,034

(22) Filed: Dec. 13, 2001

(65) Prior Publication Data

US 2002/0090637 A1 Jul. 11, 2002

Related U.S. Application Data

(60) Provisional application No. 60/255,577, filed on Dec. 14, 2000.

(51) Int. Cl.
*C12Q 1/68* (2006.01)

(52) U.S. Cl. .......................... 435/6; 536/23.1; 530/300; 436/518

(58) Field of Classification Search .................... 435/6, 435/7.9, 287.2, 91.2
See application file for complete search history.

(56) References Cited

U.S. PATENT DOCUMENTS

| | | | | |
|---|---|---|---|---|
| 6,225,047 B1 * | 5/2001 | Hutchens et al. | ............... | 435/5 |
| 2002/0090606 A1 | 7/2002 | Stewart et al. | | |

FOREIGN PATENT DOCUMENTS

| | | |
|---|---|---|
| WO | 98/59360 | 12/1998 |
| WO | 99/35502 | 7/1999 |
| WO | 99/39210 | 8/1999 |
| WO | WO 00/04389 | 1/2000 |
| WO | WO 00/39580 | 7/2000 |

OTHER PUBLICATIONS

Cai et al., PNAS USA vol. 92, pp. 6537-6541 (Jul. 1995).*
Gron et al., FEBS Lett. vol. 391 (1996) pp. 71-75.*
Holt et al. Current Opinion in Biotechnology 2000 vol. 11 pp. 445-449.*
De Kruif et al., PNAS USA vol. 92 (Apr. 1995).*
Beck et al., "Scattering of Visible Light from Silica Aerogels", J. Phys. D. Appl. Phys. 22:730-734 (1989).
Cull et al., "Preparation of Extracts from Prokaryotes", Methods In Enzymology 182:147-238 (1990).
Gygi et al., "Measuring Gene Expression by Quantitative Proteome Analysis", Curr. Opin. Biotechnol. 11:396-401 (2000).
Gygi et al., "Quantitative Analysis of Complex Protein Mixtures using Isotope-Coded Affinity Tags", Nature Biotechnology 17:994-999 (1999).
Jang et al., "Hollow Silica Spheres of Controlled Size and Porosity by Sol-Gel Processing", J. Am. Ceram. Soc. 74:1987-92 (1991).
Min Li, "Applications of Display Technology in Protein Analysis", Nature Biotechnology 18:1251-1258 (2000).
Link et al., "Direct Analysis of Protein Complexes Using Mass Spectrometry", Nature Biotechnology 17:676-682 (1999).
Link et al., "Identifying the Major Proteome Components of Haemophilus Influenzae Type-Strain NCTC 8143", Electrophoresis 18:1314-1334 (1997).
Mirgorodskaya et al., "Quantitation of Peptides and Proteins by Matrix-Assisted Laser Desorption/Ionization Mass Spectrometry using $^{18}$O-labeled Internal Standards", Rapid Commun. Mass Spectrom. 14:1226-1232 (2000).
Munchbach et al, "Quantitaiton and Faciliated de Novo Sequencing of Proteins by Isotopic N-Terminal Labeling of Peptides with a Fragmentation-Directing Moiety", Anal. Chem. 72:4047-4057 (2000).
Oda et al, "Accurate Quantitation of Protein Expression and Site-Specific Phosphorylation", Proc. Natl. Acad. Sci. USA 96:6591-6596 (1999).
Rao et al., "Effect of Gel Parameters on Monolithicity and Density of Silica Aerogels", J. Material. Science 28:3021-3026 (1993).
Ruben et al., "Imaging Aerogels at the Molecular Level" J. Materials Science 27:4341-4349 (1992).
Sanchez et al., "High-Resolution, IPG-Base, Mini Two-Dimensional Gel Electrophoresis" Methods in Mol. Bio., vol. 112:227-233, 2-D Proteome Analysis Protocols, Humana Press, Totowa, NJ (1999).
Sanchez et al., "In-Gel Sample Rehydration of Immobilized pH Gradient", Methods in Mol. Bio., vol. 112:221-225, 2-D Proteome Analysis Protocols, Humana Press, Totowa, NJ (1999).
Sanchez et al., "Preparation and Solubilization of Body Fluids for 2-D", Methods in Mol. Bio., vol. 112:87-93, 2-D Proteome Analysis Protocols, Humana Press, Totowa, NJ (1999).
Smith et al., "Cross-Linked Filamentous Phage as an Affinity Matrix", J. of Immun. Methods 215:151-161 (1998).
Washburn et al., "Large-Scale Analysis of the Yeast Proteome by Multidimensional Protein Identification Technology", Nature BioTechnology 19: 242-247 (2001).
Wilkins et al., "Protein Identification and Analysis Tools in the ExPASy Server", Methods in Mol. Bio. vol. 112:531-552, 2-D Proteome Analysis Protocols, Humana Press, Totowa, NJ (1999).
De Wildt et al., "Antibody arrays for high-throughput screening of antibody—antigen interactions" Nature Biotechnology 18:989-994 (2000).
Koivunen et al., "Identification of receptor ligands with phage display peptide libraries" Journal of Nuclear Medicine 40:883-888 (1999).
Paweletz et al., "Rapid protein display profiling of cancer progression directly from human tissue using a protein biochip" Drug Development Research 49:34-42 (2000).
Utal et al., "Preliminary expression analysis in Alzheimer's disease using SELDI protein chips" Society for Neuroscience Abstracts 26:abstracts—83.7 XP-000989844 (2000).
Coto et al. "A Preparation of A Phage DNA Based on Affinity Chromatography." Analytical Biochemistry 1993; 209: 199-201.

* cited by examiner

*Primary Examiner*—James Schultz
*Assistant Examiner*—Jeffrey S. Lundgren
(74) *Attorney, Agent, or Firm*—Clark & Elbing, LLP; Kristina Bieker-Brady

(57) ABSTRACT

Disclosed herein are methods for identifying, isolating and comparing proteins and other biomolecules differing between two complex biological samples using affinity chromatography and phage display techniques.

49 Claims, 10 Drawing Sheets

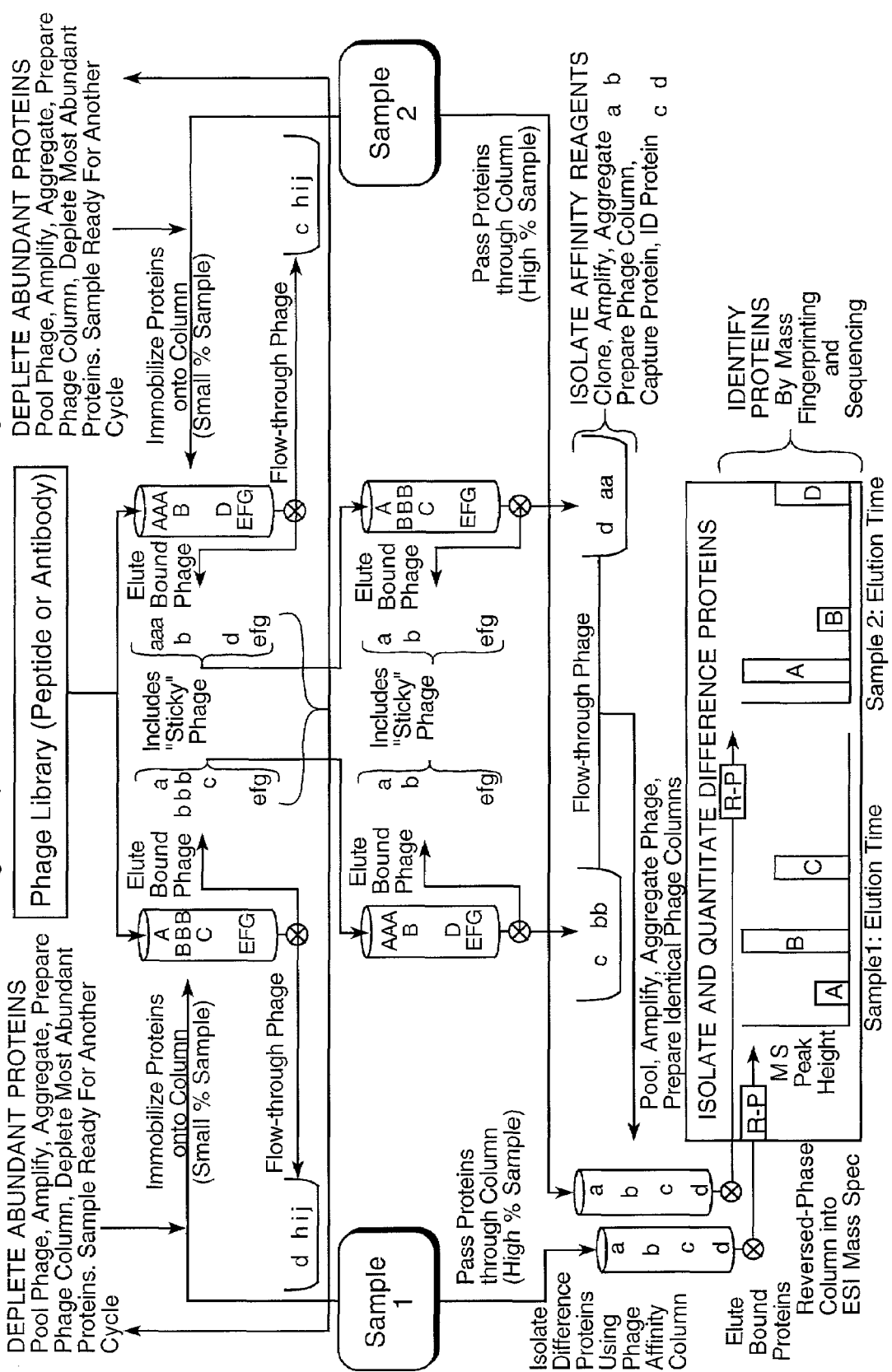
FIG. 10  Differential Phage Capture Proteomics Summary

DIFFERENTIAL PHAGE CAPTURE PROTEOMICS

CROSS REFERENCE TO RELATED APPLICATIONS

This application claims priority from U.S. Provisional Application Ser. No. 60/255,577, filed on Dec. 14, 2000.

FIELD OF THE INVENTION

The invention relates to methods for identifying and isolating proteins and other biological molecules using phage display techniques.

BACKGROUND OF THE INVENTION

There is an increasing need, particularly in the fields of medicine and agriculture, to identify and characterize the molecules which participate in a wide variety of biological processes and to find new molecules capable of modulating these processes. One way to search for novel bioactive compounds is to screen libraries of natural materials or synthesized molecules, using assay techniques which can range in complexity from simple binding reactions to elaborate physiological preparations. Unfortunately, selecting molecules of interest from large ensembles or repertoires can be time-consuming and costly, and often only provides leads which require further investigation and development.

Recently, there have been several developments both in the generation of libraries and in the methods of their selection which have improved the efficiency and effectiveness of this approach. Phage display technology, largely developed in the 1990s, is an in vitro selection technique in which a protein (or peptide) is displayed on the surface of a phage virion, while the DNA encoding the protein is contained within the virion. This direct physical linkage between the displayed protein and the DNA encoding it allows for successive rounds of selection and amplification. Large phage display libraries ("PDLs") can be generated and screened against target molecules. These PDLs may encompass an enormous number of different peptides which represent potential ligands to a variety of macromolecules such as receptors, polypeptides, enzymes, carbohydrates, and antibodies. Individual phage can be captured from the libraries by virtue of the interaction of the displayed protein with a cognate ligand, and the captured phage can be amplified by infection of bacteria. Thus, phage display technology is a very powerful tool for the selection of peptides that bind to target molecules. These peptides may find numerous applications, for example, as antigens in vaccine compositions, as enzyme inhibitors, or as agonists or antagonists of receptors.

One strategy for developing diagnostic tests and drugs for treating a disease involves the identification of key cellular components, such as proteins, that are causally related to the disease process. This can often be accomplished by looking at differences in protein composition or protein action between diseased and healthy individuals or between treated and untreated patients. Unfortunately, present methods of analyzing biomolecules are time-consuming and expensive, and suffer from inefficiencies in detection, imaging, purification, and analysis. Thus, there is a need for methods of detecting specific differences and changes between biological samples. Such methods would facilitate the identification of biological targets for diagnostic and drug development.

Although the genomics approach has advanced our understanding of the genetic basis of biological processes, it has significant limitations. For instance, the functions of products encoded by identified genes—and especially by partial cDNA sequences—are frequently unknown, and information about post-translational modifications of a protein can rarely be deduced from a knowledge of its gene sequence. It is now apparent that a large proportion of proteins undergo post-translational modifications (such as glycosylation and phosphorylation) that can profoundly influence their biochemical properties. Furthermore, protein expression is often subject to post-translational control, so that the cellular level of an mRNA does not necessarily correlate with the expression level of its gene product.

For these reasons, there is a need to supplement genomic data by studying the patterns of protein and carbohydrate expression, and of post-translational modification generally, in a biological or disease process through direct analysis of proteins, oligosaccharides, and other biomolecules. The burgeoning field of proteomics seeks to study variations in cellular protein levels between normal and diseased states by detecting and quantitating expression at the protein level, rather than the mRNA level. However, the proteomics approach faces numerous obstacles, including sample complexity, large relative abundance range, and quantitation of proteins. Technical constraints have heretofore impeded the rapid, cost-effective, reproducible, and systematic analysis of proteins and other biomolecules present in biological samples.

SUMMARY OF THE INVENTION

The present invention features methods for isolation and quantitation of proteins and other biomolecules differing between samples over a wide range of relative abundance. The invention provides for the identification of proteins as known species, or as species with novel sequence or novel post-translational modifications, and supplies a means for characterization and isolation of specific affinity reagents against such proteins.

In one aspect, the invention provides a method of identifying a protein, polypeptide or other biomolecule that involves (a) adhering a complex biological sample from a first type of individual to a support to create an array; (b) adhering a complex biological sample from a second type of individual to a support to create an array; (c) exposing a peptide-nucleic acid coupled library at least one time to an array formed by step (a) to create a first product; and (d) exposing the first product at least one time to an array formed by step (b) to create a second product.

In one embodiment of the invention, the method further includes the steps of (e) exposing a peptide-nucleic acid coupled library at least one time to an array formed by step (b) to create a third product; and (f) exposing the third product at least one time to an array formed by step (a) to create a fourth product. The second and fourth products may be compared, preferably via mass spectrometry, to identify differences between the two biological samples.

In another embodiment, the method includes the following additional steps: (g) combining the second and fourth products to produce a pooled product; (h) amplifying the pooled product; (i) adhering a portion of the amplified pooled product to a support to provide an array; (j) exposing a complex biological sample from the first or second type of individual at least one time to an array formed by step (i) to provide a fifth product; (k) exposing a complex biological sample from the first or second type of individual at least one time to an array formed by step (i) to provide a sixth product, wherein the complex biological sample is from a type of individual which is different from that used in step (j); and (l) comparing said fifth product and the sixth products. In a preferred embodiment, these products are compared using mass spectrometry.

The method of the invention allows for the identification of differences between two biological samples by using affinity chromatography and phage display techniques. With this method, a sample taken from a diseased individual can be compared against a sample taken from a non-diseased individual to identify differences in the expression of biomolecules within the two samples. Samples from medicated and non-medicated individuals can likewise be compared. The identification of differences between such samples can lead to biological targets and information useful for diagnostic and/or pharmaceutical development.

The biological samples to be compared can be taken from a wide variety of biological sources, including tissues, such as epithelial, connective, muscle, or nerve tissue, or cultured cell types derived therefrom. Alternatively, the biological samples may be taken from a body fluid, such as cerebrospinal fluid (CSF), blood, saliva, mucous, tears, pancreatic juice, seminal fluid, sweat, milk, bile, plasma, serum, lymph, urine, pleural effusions, bronchial lavage, ascites, or synovial fluid. In a particularly preferred embodiment, the body fluid is CSF.

In yet another embodiment, the biological samples are from an organ type, including skin, bone, cartilage, tendon, ligament, skeletal muscle, smooth muscle, heart, blood, blood vessel, brain, spinal cord, peripheral nerve, nose, trachea, lung, mouth, esophagus, stomach, intestine, kidney, uterus, ureters, urethra, bladder, hypothalamus, pituitary, thyroid, pancreas, adrenal gland, ovary, oviduct, vagina, mammary gland, testicle, seminal vesicle, penis, lymph, lymph node, lymph vessel, white blood cell, T-cell and B-cell.

The arrays of the invention can be prepared by crosslinking the complex biological samples to a solid support. The samples are preferably treated with chemical agents to denature the proteins prior to being adhered to the support.

In a preferred embodiment of the invention, the peptide-nucleic acid coupled library is a phage display library, most preferably an antibody library, or a recombinant display or synthetic peptide library.

The various products formed by exposing a library or complex biological sample to an array may include either material which did not bind to the array (i.e., flow-through product) or material which bound to the array and was subsequently released (i.e., eluted bound product). The library or complex biological sample may be exposed to the array multiple times in order to produce the product.

Other features and advantages of the invention will be apparent from the following detailed description thereof and from the claims.

DEFINITIONS

By "adhering" is meant directly or indirectly linking a portion of one material to a portion of another material, either covalently or non-covalently.

By "amplifying" is meant increasing in number.

By "array" is meant a plurality of polymer sequences (e.g. proteins, peptides, oligonucleotides, polynucleotides, etc.) or other biomolecules which are associated with the surface of a substrate or support. Examples of arrays include a protein affinity column and a phage affinity column.

By "complex biological sample" or "biological sample" is meant any solid or fluid sample obtained from, excreted by, or secreted by any living organism, including single-celled micro-organisms (such as bacteria and yeast) and multicellular organisms (such as plants and animals, for instance a vertebrate or a mammal, and in particular a healthy or apparently healthy human subject or a human patient affected by a condition or disease). A biological sample may be a biological fluid obtained from any site or substance of the organism (e.g. blood, plasma, serum, urine, bile, cerebrospinal fluid, aqueous or vitreous humor, or any bodily secretion), a transudate, an exudate (e.g. fluid obtained from an abscess or any other site of infection or inflammation), or fluid obtained from a joint (e.g. a normal joint or a joint affected by disease such as rheumatoid arthritis, osteoarthritis, gout or septic arthritis). Alternatively, a biological sample can be obtained from any organ or tissue (including a biopsy or autopsy specimen) or may comprise cells (whether primary cells or cultured cells) or medium conditioned by any cell, tissue or organ. If desired, the biological sample may be subjected to preliminary processing, including but not limited to preliminary separation techniques and/or denaturation. For example, cells or tissues can be extracted and subjected to subcellular fractionation for separate analysis of biomolecules in distinct subcellular fractions, e.g. proteins or drugs found in different parts of the cell. See Deutscher (ed.), *Methods In Enzymology* 182: 147–238 (1990). Similarly, immunoprecipitation can be performed to identify antigenically related biomolecules such as proteins.

By "exposing" is meant allowing contact to occur between two materials.

By "individual" or "subject" is meant a single-celled or multicellular organism, such as a plant, animal, fungus, protozoan, or bacterium. In a preferred embodiment, the individual is a mammal, most preferably a human or other primate species.

By "peptide-nucleic acid coupled library" is meant a collection of peptides wherein each peptide is linked (directly or indirectly) to the DNA that encodes the peptide. An example of a peptide-nucleic acid coupled library would be a phage display library ("PDL").

The terms "peptide", "protein" and "polypeptide" are used interchangeably herein and refer to any chain of two or more amino acids joined to each other by peptide bonds or modified peptide bonds, regardless of post-translational modification (e.g., glycosylation or phosphorylation).

The present invention is useful for identifying and analyzing proteins, but is more generally applicable to the identification and analysis of any biomolecule. As used herein, the term "biomolecule" refers to any organic molecule that is present in a biological sample, and includes peptides, polypeptides, proteins, fatty acids, oligosaccharides, lipids, steroids, prostaglandins, prostacyclines, and nucleic acids (including DNA and RNA).

By "substrate" or "support" is meant any porous or non-porous water insoluble material, which is preferably rigid or semi-rigid. The surface can have any one of a number of shapes, such as membranes, filters, chips, slides, wafers, fibers, magnetic or nonmagnetic beads, gels, tubing, strips, plates, rods, polymers, particles, microparticles, capillaries, and the like. The substrate can have a variety of surface forms, such as wells, trenches, pins, channels and pores, to which polypeptides, polynucleotides, or other biomolecules are bound. The substrate can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly (4-methylbutene), polystyrene, polymethacrylate, poly(ethylene terephthalate), nylon, poly(vinyl butyrate), etc.; either used by themselves or in conjunction with other materials; glass available as Bioglass, ceramics, metals, and the like. Natural or synthetic assemblies such as liposomes, phospholipid vesicles, and cells can also be employed. A commonly used support is Controlled Pore Glass (CPG), which consists of a glass matrix prepared uniformly with pores of defined size. Immobilization of proteins and other biomolecules on a substrate or surface may be accomplished by well-known techniques, commonly available in the literature.

BRIEF DESCRIPTION OF THE DRAWINGS

FIG. 10 is a schematic diagram summarizing the process of differential phage capture proteomics as illustrated in FIGS. 1–9.

DETAILED DESCRIPTION

Figure 1:
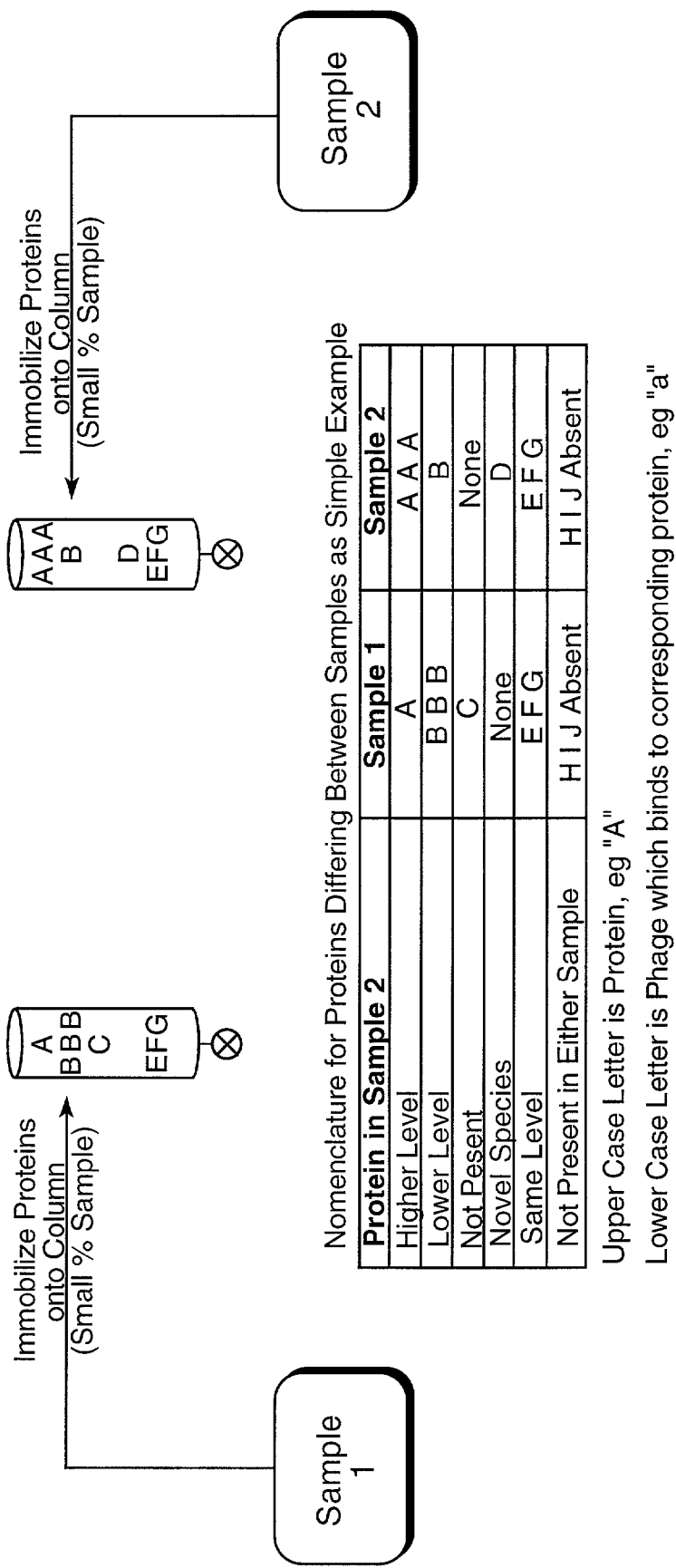
FIG. 1 is a schematic diagram showing the preparation of protein affinity matrices from two different biological samples.

In developing new methods for diagnosing and treating a disease, it is important to identify the key cellular components, such as proteins and other biomolecules, that are associated with the disease. One way to identify such components is to look for differences in protein expression between diseased and healthy individuals.

The present invention provides a means for comparing two complex biological samples in order to determine the differences in proteins and other biomolecules that are present in the samples. In a preferred embodiment, a pair of protein affinity matrices are prepared from the two biological samples to be compared. A phage display library is exposed to the matrices in a series of capture steps which results in the isolation of phage that bind to those proteins that are different between the two samples (i.e. the "difference proteins"). These phage are amplified and used to prepare a set of phage affinity matrices. The biological samples being compared are then exposed to these phage matrices in order to capture differentially expressed proteins. By comparing a sample taken from a diseased subject to a sample taken from a healthy subject, one can identify biological targets of therapeutic and diagnostic importance and lead structures for drug development. For example, a receptor that is found to exist on only a sample taken from a diseased individual, or at a different concentration in the diseased sample, may serve as a potential target for diagnosis or treatment of the disease. In addition, a ligand found to have high affinity and specificity for the receptor provides a lead structure for drug development. Furthermore, a protein species which changes its distribution, level, or characteristics during treatment may provide an indication of beneficial or toxic effect in an animal, such as a human patient.

Samples can be taken from a wide variety of organs types, including but not limited to skin, bone, cartilage, tendon, ligament, skeletal muscle, smooth muscle, heart, blood, blood vessel, brain, spinal cord, peripheral nerve, nose, trachea, lung, mouth, esophagus, stomach, intestine, kidney, uterus, ureters, urethra, bladder, hypothalamus, pituitary, thyroid, pancreas, adrenal gland, ovary, oviduct, vagina, mammary gland, testicle, seminal vesicle, penis, lymph, lymph node, lymph vessel, white blood cell, T-cell and B-cell. Other suitable sample sources include, but are not limited to, epithelial, connective, muscle, or nerve tissue, or bodily fluids, such as cerebrospinal fluid (CSF), blood, saliva, tears, mucous, pancreatic juice, seminal fluid, sweat, milk, bile, plasma, serum, lymph, urine, pleural effusions, bronchial lavage, ascites, or synovial fluid.

The source of the sample is chosen based on a variety of factors, such as the nature of the disease or condition being studied. For instance, CSF may be taken to study a disease of the central nervous system, while pancreatic juice may be taken to study a disease of the pancreas. In a disease state such as cancer, any or all of the types of tissues or cells which are related directly to the particular type of cancer (e.g. lymph for lymphoma, etc.) may be analyzed. Methods for properly collecting and storing various biological samples are known in the art, and may vary depending on the nature of the sample.

Preparation of Affinity Matrices Using Biological Samples

After the biological samples have been collected, a set of arrays or matrices are created by adhering each of the samples to a separate support (FIG. 1). In one embodiment of the invention, the array is an affinity matrix that includes a solid support or gel to which is attached a multiplicity of different proteins or other biomolecules. Suitable matrix materials include, but are not limited to paper, glasses, ceramics, metals, metalloids, polacryloylmorpholide, various plastics and plastic copolymers such as NYLON™, TEFLON™, polyethylene, polypropylene, poly(4-methylbutene), polystyrene, polystyrene, polystyrene/latex, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and controlled-pore glass (Controlled Pore Glass, Inc., Fairfield, N.J.), aerogels (see, e.g., Ruben et al., J. Materials Science 27:4341–4349 (1992); Rao et al., J. Material. Science 28:3021 (1993); Back et al., J. Phys. D. Appl.

Phys. 22:7309–734 (1989); Kim & Jang, J. Am. Ceram. Soc. 74:1987–92 (1991) and the like, and other materials generally known to be suitable for use in affinity columns. In a preferred embodiment, the support is a streptavidin sepharose column. However, screening can be carried out on other solid phases or in solution.

Biomolecules, such as proteins, can easily be attached to a solid substrate where they act as immobilized ligands that interact with complementary molecules present in a solution contacted to the substrate. The source to be screened, for example a phage display library, is passed over the affinity matrix, allowing target molecules to be captured by the immobilized ligands. Unbound components can be washed away from the bound complex to either provide a solution lacking the target molecules bound to the affinity column, or to provide the isolated target molecules themselves. After unbound background substances are washed away, the bound material is eluted, often in an eluent that loosens the association between the target and the ligand. The biomolecules captured in a affinity matrix can be separated and released by denaturation either through heat, adjustment of salt concentration, or the use of a destabilizing agent such as formamide, TWEEN™-20 denaturing agent, or sodium dodecyl sulfate (SDS).

Many techniques are known in the art for attaching proteins and other biomolecules to a substrate or support, such as those described in, for example, *Bioconjugation: Protein Coupling Techniques for the Biomedical Sciences*, M. Aslam, A. Dent Groves Dictionaries, Inc. New York, N.Y. (1988). Any suitable derivatization or solid phase binding method may be used. In a preferred embodiment, the proteins of the complex biological sample are adhered by biotinylating the proteins and using a substrate or support that includes avidin or an avidin-related compound (e.g. streptavidin). The biotin specifically binds to the avidin-related compound thereby attaching the proteins to the substrate. Other well known specific binding pairs may also be used as a means for attaching the sample proteins to the support.

Prior to adhering the samples to the support, the proteins of the sample may be denatured to allow for a more complete analysis. A variety of dissociative methods are known in the art and may be used to break up protein complexes, solubilize proteins, and unfold proteins within the samples. These methods include, for example, treatment with guanidine HCL, formic acid, various chaotropes, detergents, heating, phase partitioning, and derivatization. Alternatively, if the associations of proteins in the sample are to be preserved, such treatments are omitted and the protein complexes may optionally be crosslinked to increase stability. By preserving associations, phage against one member of a protein complex may allow for the isolation and identification of more than one component of a complex.

Peptide-Nucleic Acid Coupled Libraries

In accordance with the present invention, the protein affinity matrices described above are used to screen a peptide-nucleic acid coupled library, which is made up of a collection of peptides, wherein each peptide is linked to the DNA encoding it. In a preferred embodiment, the library is a phage display library. Display technology represents a collection of methods for creating libraries of modularly coded biomolecules that can be screened for desired properties. Two of the most important characteristics of display technologies are extremely high detection sensitivity and the ability to determine the structure of a desired compound rapidly after initial screening. A variety of phage libraries can be used, in the present invention, including immune or nonimmune, and single-chain Fv or Fab fragment antibody libraries; and recombinant-display or synthetic peptide libraries. Examples of suitable phage display libraries and techniques for their preparation are well known in the art and described in, for example, Barbas, F., et al., *Phage Display: A Laboratory Manual*, Cold Spring Harbor, N.Y. (2001). Other libraries which can be used are described by Li, M., "Applications of display technology in protein analysis", *Nature Biotechnology* 18:1251–1258 (2000).

Peptide libraries comprise vast numbers of peptides of a given length, whose sequences have been randomly generated to vary the amino acid residues at each position. The usual goal for using such libraries is to select high affinity binders from the typical pool of binders that is found against nearly all proteins that are screened. In its simplest form, the method of the invention uses a single binder of moderate/low affinity, which is selected during the process for optimal protein capture and release.

Phage display libraries can be selected based on their particular properties, depending on the type of analysis required and the properties of the affinity reagents to be isolated. For example, the choice between peptide and antibody phage display libraries related to whether a desired affinity reagent is a peptide or an antibody. The library used preferably contains as large and diverse a population of binders specific for the chosen sample as possible. Compatible mixtures of libraries can be used to capture as many species as possible from the chosen sample. Ultimately, "panproteomic" and "proteomic subset" libraries can be developed which contain binders for all known species in any particular type of sample.

Figure 2:
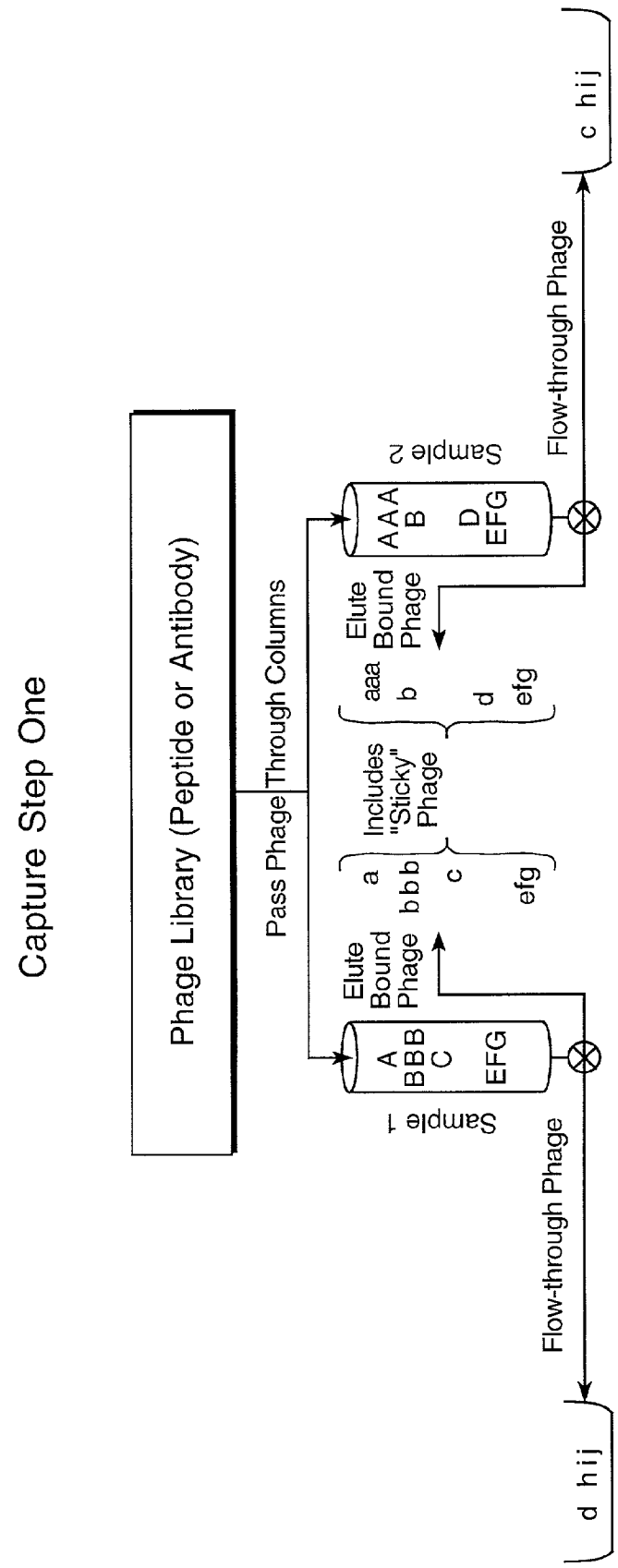
FIG. 2 is a schematic diagram showing an initial capture of phage by the protein affinity matrices.
Figure 3:
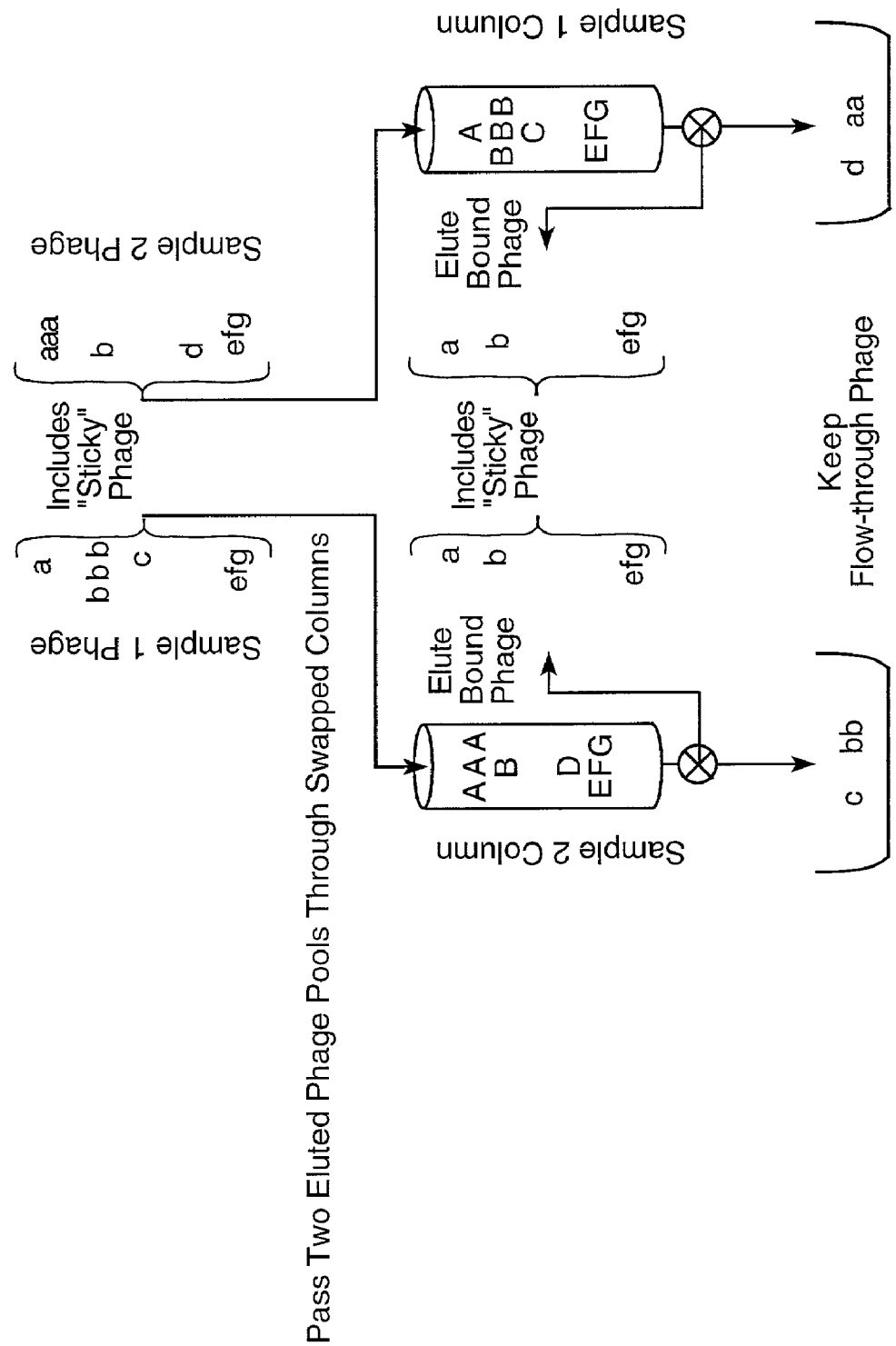
FIG. 3 is a schematic diagram showing a subsequent capture step, in which phage that were captured by the first affinity column are then run through the second column, and vice versa.

The phage library is passed through the protein affinity matrices generated from two different biological samples in order to capture phage that bind the proteins that differ between the two samples. The sequence of phage exposure is shown in FIGS. 2 and 3. First, the phage library is exposed to a protein affinity matrix prepared from the first biological sample. The unbound phage is washed away, and the bound phage is released and then exposed to a protein affinity matrix prepared from the second biological sample. The flow-through from this second exposure step is retained and contains phage that bind to proteins present in the first biological sample but not the second sample.

An identical phage library is exposed to the affinity matrices in the reverse order, i.e., the library is first exposed to a protein affinity matrix prepared from the second sample. The unbound phage is washed away and the bound phage is eluted and then exposed to a protein affinity matrix prepared from the first sample. The flow-through from the second exposure step is retained and contains phage that bind to proteins present in the second sample, but not the first sample.

Thus, the phage library goes through two capture steps. In the first step, the phage library is passed through the protein affinity matrices prepared from the biological samples and the bound phage are recovered. In the second capture step, the phage which bound to the protein affinity matrix prepared from the first sample, are exposed to the protein affinity matrix prepared from the second sample. Conversely, phage which bound to the protein affinity matrix prepared from the second sample, are exposed to the protein affinity matrix prepared from the first sample. This combination of capture steps results in the isolation of phage that are capable of binding to those proteins which are different between the first and second samples. The flow-through phage from the second capture step may be pooled, amplified, and used to prepare a set of identical phage affinity matrices for further screening. In addition, the phage may be used to isolate affinity reagents against the "difference proteins" (See FIG. 7).

Phage Affinity Matrices

Figure 4:
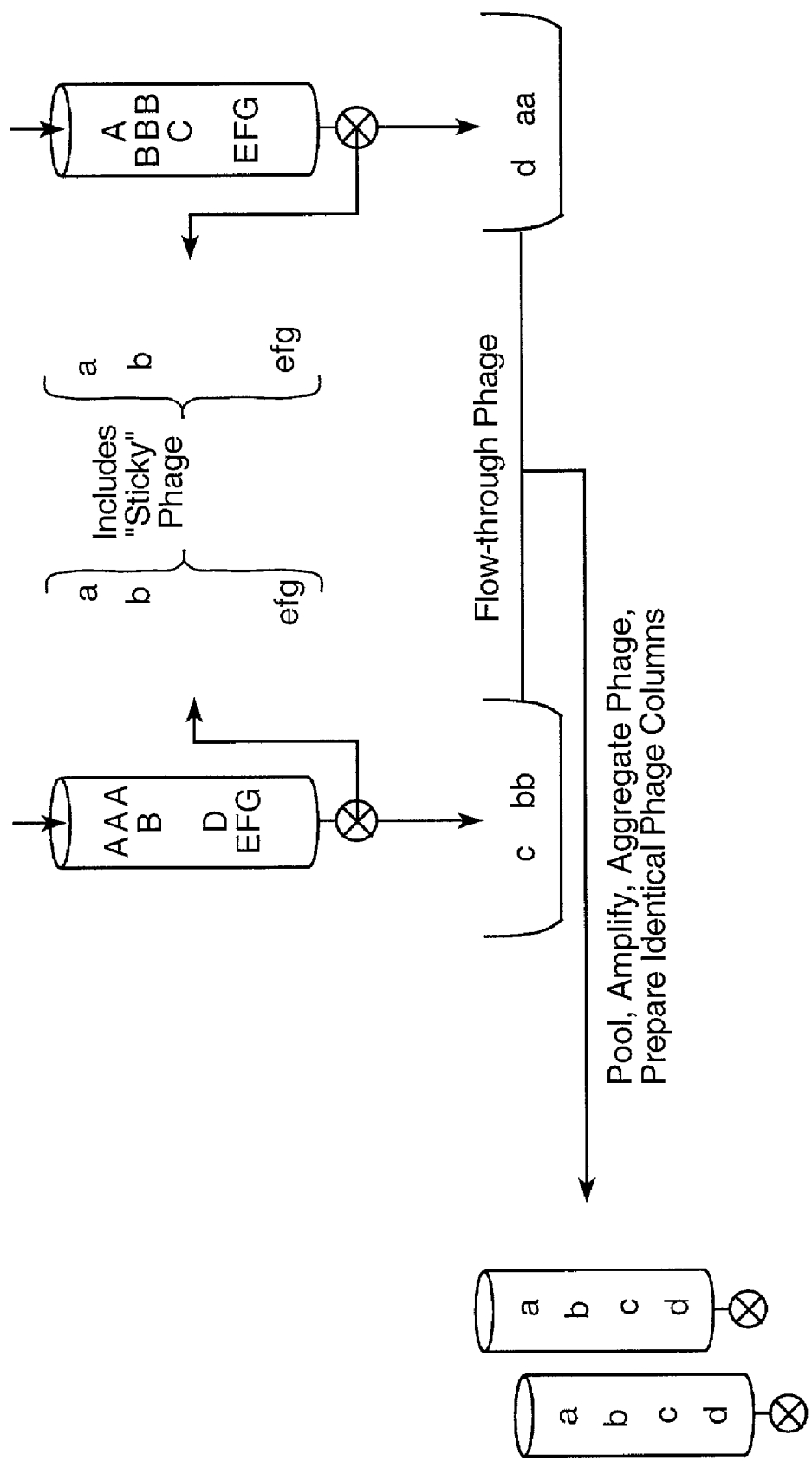
FIG. 4 is a schematic diagram showing the preparation of a set of phage affinity matrices by pooling and amplifying the flow-through phage.

As discussed above, the phage which have been selected from the phage display library by exposure to protein affinity matrices are used to generate a set of phage affinity matrices (FIG. 4). Methods for preparing phage as an affinity matrix are known in the art and described, for example, by Smith et al., *Journal of Immunological Methods* 215:151–161 (1998). These phage affinity matrices can be used to directly screen the biological samples being compared. Prior to passing the samples through the phage matrix, they may be treated, as discussed above, using any of a variety of dissociative methods to break up protein complexes, solubilize proteins, and unfold proteins to allow a more complete analysis. Cross-linked filamentous phage can be successfully employed directly for affinity purifications, and the direct use of aggregated phage encoding an affinity capture peptide avoids the need to decode the appropriate peptide sequence, synthesize it and then prepare an affinity capture matrix, although this can be done if desired.

Figure 5:
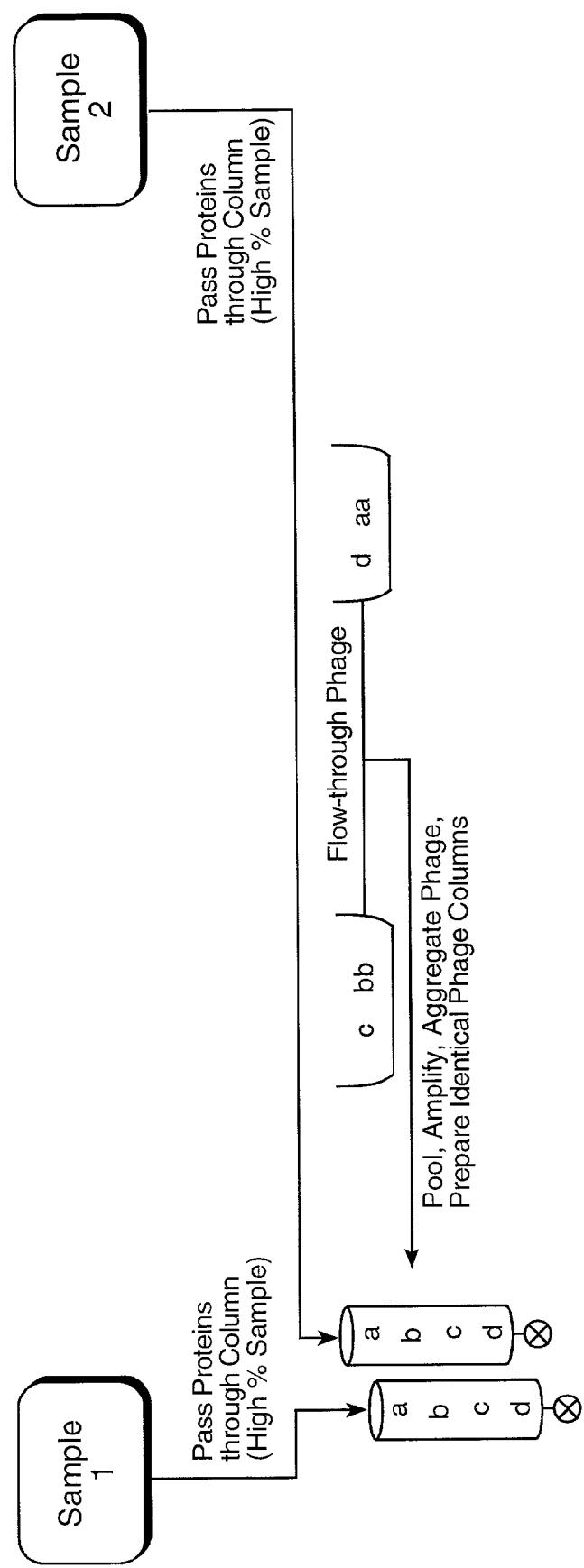
FIG. 5 is a schematic diagram showing a third capture step in which complex biological samples from two different individuals are passed through a set of phage affinity matrices/columns.

As shown in FIG. 5, complex biological samples from two different individuals are exposed to the phage affinity matrices. The proteins that bind to the phage matrices include those proteins which are different between the two samples. Proteins which fail to bind to the phage matrices are washed away and the bound proteins are eluted and analyzed (FIG. 6), using any of a variety of identification and quantitation methods known in the art. (See Gygi, S. P., et al., *Nature Biotechnology* 17:994–999 (1999); Gygi, S. P., et al., Curr. Opin. Biotechnol 11:396–401 (2000); Oda, Y, et al, *Proc. Natl. Acad. Sci.* USA 96:6591–6596 (1999); Mirgorodskaya, O. A., et al., *Rapid Commun. Mass Spectrom.* 14:1226–1232 (2000); Munchbach, M., et al, *Anal. Chem.* 72:4047–4057 (2000); Link, A. J. et al., *Electrophoresis* 18:1314–1334 (1997); Washburn et al., *Nature BioTechnology* 19: 242–247 (2001)). In a preferred embodiment, the eluted proteins are passed through a reverse phase column into an ESI mass spectrometer. The proteins are identified by mass fingerprinting and sequencing. In addition to identifying proteins that are present in one sample but not the other, one skilled in the art will appreciate that the method of the invention can also be used to determine differing levels of a protein between two samples.

Depletion of Most Abundant Proteins

Figure 8:
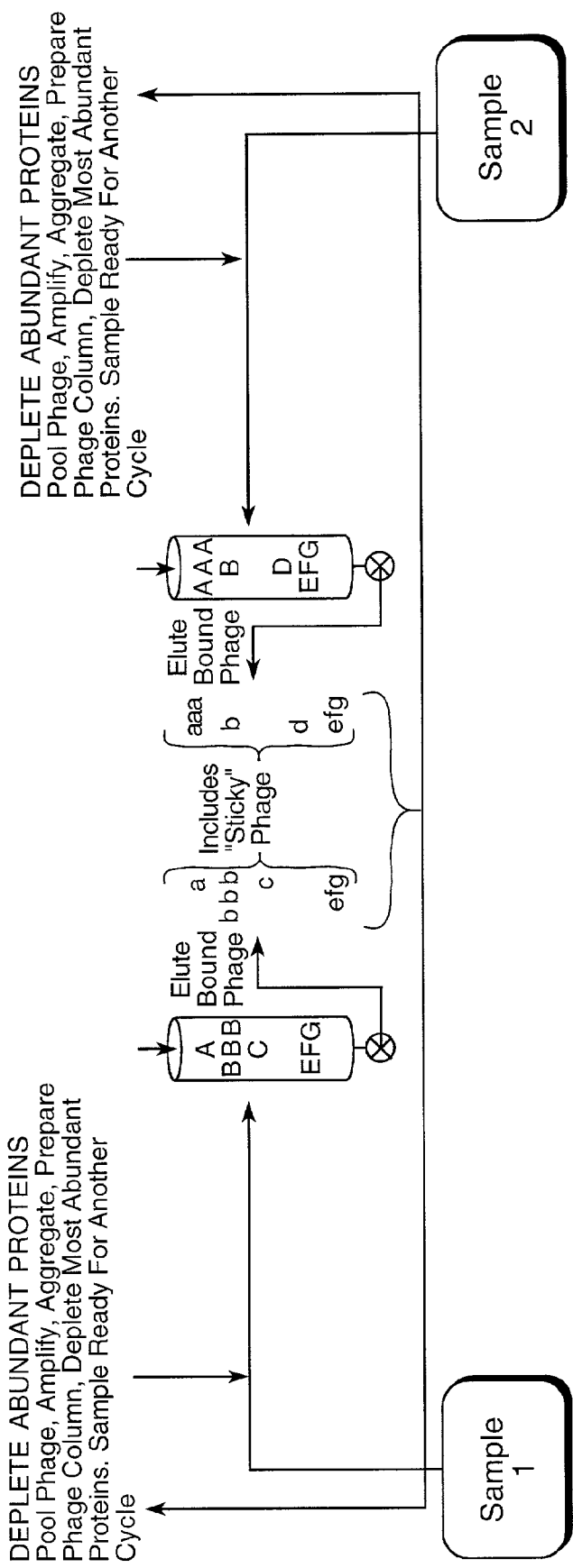
FIG. 8 is a schematic diagram showing a cycle for depletion of the most abundant proteins within two different complex biological samples.

As shown in FIG. 8, in one embodiment of the invention, the most abundant proteins contained within the biological samples can be depleted by recovering the bound phage after the initial capture step (FIG. 2), amplifying the phage, preparing phage affinity columns, and repeating the cycle using the methods described above and in the Example below. The steps shown in FIGS. 8 and 9 can be continuously repeated until the limits of detection of the analytical device have been reached. Once the abundant proteins have been depleted, the differences in the biological samples can be analyzed according to the techniques described herein, using samples containing less abundant proteins. This allows for identification of proteins which may be present in very low quantities in the biological samples.

The present invention is illustrated by the following example which describes an application of the method of the present invention to a pair of samples of human cerebrospinal fluid (CSF). The example is in no way intended to be limiting of the invention.

EXAMPLE

Step I. Proteins Capture Phage Against Proteins Differing Between Samples (a) Preparation of Protein Affinity Matrices for Two Samples (FIG. 1).

Sample Collection. Samples of human CSF are collected from two different individuals by lumbar puncture in a sterile container. The samples should immediately be placed in an ice bath and brought to the laboratory for analysis. On arrival in the laboratory, the CSF samples should be centrifuged to remove circulating cells at 2,000 g for 10 minutes at 5° C. The samples can be either processed immediately or stored at −7° C. until analysis (Sanchez, J. C. and Hochstrasser, D. F., "Proteome Analysis Protocols" in *Methods in Molecular Biology*, Vol. 112, Humana Press, Totowa, N.J. (1999)).

Sample Preparation. To dissociate bound proteins and other species, and to minimize protein interactions, aliquots of the samples (100 μl) are made up to a final concentration of 3M guanidine HCl and 0.2M formic acid, and incubated in ice for 60 minutes. They are then buffer exchanged using a HiTrap Desalting Column (Amersham Pharmacia Biotech) on an HPLC system at a flow rate of 5 ml/min with phosphate-buffered-saline (PBS) and collected in a final volume of 200 μl. The low molecular weight flow-through can be passed through a SepPak column and washed with PBS to isolate peptides for additional analysis if desired. If the in vivo associations of proteins are to be preserved, then the additions of guanidine HCl and formic acid are omitted, and the CSF aliquots are diluted 1:2 with PBS before the next step.

Protein Biotinylation. In the next step, the proteins in the buffer exchanged samples are biotinylated. Immediately prior to use, make a 0.5 mg/ml solution of Sulfo-NHS-LC-Biotin in 2 mM sodium acetate, pH 6.0. Add 50 μl of this solution to the desalted CSF sample and incubate in ice for 2 hours. Add 500 μl 1M Tris-HCl, pH 7.4, and incubate for a further 30 minutes to inactivate the remaining biotin linker. To remove unreacted biotin, desalt using a HiTrap Desalting Column (Amersham Pharmacia Biotech) on an HPLC system at a flow rate of 5 ml/min with TBS (50 mMTris-HCl, pH 7.5, 150 mM NaCl) and collect in a final volume of 200 μl (Barbas, F., et al., *Phage Display: A Laboratory Manual*, Cold Spring Harbor, N.Y. (2001)).

Capture Column Preparation. Pass a biotinylated and desalted solution from a human CSF sample, named Sample 1, over a HiTrap Streptavidin Sepharose Column (Amersham Pharmacia Biotech) on an HPLC system equilibrated with TBS at 0.1 ml/minute. Wash this column ("Column 1"), with 20 ml of TBS at 1.0 ml/minute. Repeat this process for a second human CSF sample, named Sample 2, to yield a second column ("Column 2").

(b) Capture Step One (FIG. 2)

Proteins Capture Phage. Pass $10^3$ to $10^4$ equivalents of a Phage Peptide Library (eg $2\times10^{11}$ particles for a library of $2\times10^8$ clones would be $10^3$ equivalents) in 5 ml of TBS over each of Columns 1 and 2 on an HPLC system, at a flow rate of 40 μl/minute. Wash the columns with 20 ml TBS at a flow rate of 0.5 ml/minute.

Captured Phage are Eluted. Elute the bound phage with 1 ml Panning Elution Buffer (0.1 M HCl adjusted to pH 2.2 with glycine) at a flow rate of 0.5 ml/minute and collect fractions. Pool the fractions containing phage, buffer exchange using a HiTrap Desalting Column (Amersham Pharmacia Biotech) on an HPLC system at a flow rate of 5 ml/min with TBS, and collect in a final volume of about 1 ml. (Barbas, F. et al., *Phage Display: A Laboratory Manual*, Cold Spring Harbor, N.Y. (2001)).

(c) Capture Step Two (FIG. 3)

Proteins Capture Phage from Swapped Columns. Pass the eluted and buffer exchanged phage from Column 1 over Column 2 on an HPLC system, at a flow rate of 40 µl/minute. Wash the column with 20 ml TBS at a flow rate of 0.5 ml/minute. Repeat this process with the eluted and buffer exchanged phage from Column 2 over Column 1.

Captured Phage from Swapped Columns are Eluted. Elute the bound phage from Column 1 with 1 ml Panning Elution Buffer (0.1 M HCl adjusted to pH 2.2 with glycine) at a flow rate of 0.5 ml/minute and collect fractions. Pool the fractions containing phage, and neutralize with about 140 µl 1M Tris Base, pH 9.1. Verify the pH has been raised to yield a solution of pH 7.0–8.2. Repeat this process with the bound phage from Column 2.

Step II. Specific Phage Capture Difference Proteins (a) Preparation of Phage Affinity Matrix (FIG. 4)

Pool Phage. Pool the flow-through phage from Columns 1 and 2.

Amplify Phage. Cells for Phage Infection are prepared according to the following protocol:

1. Transfer a single colony of K91 cells to a culture tube containing 2 ml of NZY. Incubate overnight at 37° C. with vigorous shaking (250 rpm).

2. Inoculate a 125-ml flask containing 20 ml of NZY with 400 µl of the overnight culture. Shake vigorously (250 rpm) at 37° C. until the cells have reached mid-log phase ($OD_{595}$=~0.45; this takes about 1.5–2 hours).

3. Use slow shaking to 100 rpm for 10 minutes to allow the bacteria to regenerate sheared F. pili. Measure the $OD_{595}$; it preferably should not be over 0.65 (best at 0.55–0.65).

4. Transfer the culture to an Oak Ridge tube and centrifuge at 600 g (2,200 rpm) in a SORVALL SS34 rotor (or equivalent) for 10 minutes at room temperature or 4° C.

5. Discard the supernatant and gently resuspend the cells in 20 ml of 80 mM NaCl.

6. Transfer the mixture to a 125-ml culture flask and shake gently (100 rpm) at 37° C. for 45 minutes.

7. Transfer the mixture to an Oak Ridge tube and centrifuge at 850 g (2,800 rpm) in an SS34 rotor (or equivalent) for 10 minutes at 4° C.

8. Pour off the supernatant and resuspend the cells gently in 1 ml of 4° C. NAP buffer.

9. Keep the cells on ice when in use, and store on ice in the refrigerator. The cells are best used immediately, but will stay competent for phage infection for a few days. The cells are no longer competent if they remain aggregated after gently shaking of the tube in which they are stored. The final concentration of cells should be approximately $5 \times 10^9$ cells/ml. (Barbas, F. et al., *Phage Display: A Laboratory Manual*, Cold Spring Harbor, N.Y. (2001)).

Infect the Starved Cells With Eluted Phage.

1. Determine the concentration of the phage by agarose gel electrophoresis or spectrophotometry.

2. Infect cells by distributing 10 µl of diluted virions (less than or equal to $10^6$ particles) into microcentrifuge tubes or into wells across a row of a flexible ELISA plate. Add 10 µl of starved or fresh, high-density cells (~$5 \times 10^7$ cells). Incubate at room temperature for 10–15 minutes.

3. Induce the tetracycline-resistance genes by adding 150 µl (for microtiter plates) to 1 ml (for microcentrifuge tubes) of NZY containing 0.2 µg/ml tetracycline and mixing.

Incubate at 39° C. with intermittent shaking (or tapping the ELISA plate) for 30 minutes. If using 1.5 ml microcentrifuge tubes, place the tubes upside-down in a beaker and shake in an incubator. Briefly microfuge the tubes before opening, and mix the cells by pipetting.

4. Dilute the infected cells in flexible microtiter plates with NZY containing 15 µg/ml tetracycline. Mix 20 µl of cells with 180 µl of NZY+tet for 1:10 dilutions, and 2 µl in 198 µl of NZY+tet for 1:1000 dilutions.

5. The concentration of tetracycline-resistant transducing units (TU) is determined by titering. Titering of an unknown sample is usually done alongside cells infected with a positive control phage whose number of particles/ml is known and that has been previously titered. A good positive control is a stock of CsCl-purified fd-tet or f88-4 phage. Cells that have been treated with phage-dilution buffer alone, in parallel with the diluted phage samples, serve as the negative control. When counting colonies, 1 colony=1 TU.

6. For plate titering, spread 100 µl of diluted, infected cells onto NZY agar plates containing 40 µg/ml tetracycline. Spread one plate per dilution. Invert the plates and incubate overnight at 37° C.

7. For spot titering, use plates that have been dried by incubating them with their lids askew in a 37° C. incubator or sterile hood for a few hours. Before spotting, mark the plates where each spot (up to 16 per plate) will go. Carefully dot 15–20 µl of diluted phage over each spot (a multichannel pipettor can be used for this). Let the agar absorb the drops (the spots should become flat), then invert the plates and incubate overnight at 30° C.

8. For colony counting (especially from spot titers), the tetracycline-resistant colonies should be small, but visible. To prevent the overgrowth of colonies, (1) take the plates out of the 37° C. incubator before leaving for the night, let them sit overnight at room temperature, and put them back at 37° C. the following day until the colonies reach the right size; or (2) if the infections are done late at night, incubate overnight at 30° C. and have someone check the colonies at the beginning of the following day. Once the colonies have reached optimal counting size, they should be stored at 4° C. until they are counted. They can be stored for several weeks if the plates are sealed with Parafilm. (Barbas, F. et al., *Phage Display: A Laboratory Manual*, Cold Spring Harbor, N.Y. (2001)).

Large-Scale Preparation of Phage

1. Pick all single transfected colonies and mix each in a 1.5 ml microcentrifuge tube containing 220 µl of NZY medium. Pool contents of all tubes, and inoculate each of two 2-liter flasks containing 500 ml of NZY and 15 µg/ml of tetracycline with the diluted, pooled cells. Shake vigorously (~200 rpm) for about 20 hours at 37° C.

2. Transfer 100 µl of culture to a 0.5 ml microcentrifuge tube, and pellet the cells in a microfuge by spinning full-speed (14,000 rpm) for 2 minutes. Transfer 20 µl of the phage-containing supernatant to a fresh 0.5 ml microcentrifuge tube containing 5 µl of 5×Lysis Mix (warm the Lysis Mix to make sure the SDS is in solution); mix by pipetting. Incubate tube in a 70° C. water bath for 15–20 minutes and microfuge briefly. Load a 15 µl sample onto a 0.8% agarose gel in 4×GBB, and run. Use a known quantity of f88.4 phage as a control ($2 \times 10^{10}$ phage particles=100 ng DNA). Run this gel either before going on in the procedure (to be sure the phage yield is good; ~$10^{12}$ particles/ml of culture supernatant), or at the end of the procedure (to determine the percent yield of PEG-purified phage).

3. Divide the culture from Step 1 among four 250-ml centrifuge bottles (~230 ml/bottle) Centrifuge at 2,400 g for 10 minutes at 4° C. Without disturbing the cell pellet, transfer the phage-containing supernatant into clean bottles, and recentrifuge at 6,200 g for 10 minutes at 4° C. Carefully pour the supernatant into fresh, tared, 250 ml centrifuge bottles and determine the culture volume in each bottle (1 g=1 ml).

4. Add 0.15 volume of PEG/NaCl solution to each bottle of measure supernatant. Screw caps on tightly, and mix thoroughly by inverting the bottles gently approximately 100 times. Incubate the mixtures for at least 4 hours on ice or overnight at 4° C.

5. Pellet the phage by centrifuging at 6,200 g for 40 minutes at 4° C. Discard the supernatant, being careful not to disturb the pellet. Remove the residual supernatant by briefly recentrifuging the bottles, tilting each bottle so that the pellet is opposite the remaining supernatant, and aspirating with a 1-ml pipettor.

6. Add 7.5 ml of TBS to each bottle and shake at 150 rpm in a 37° C. incubator for approximately 30 minutes to resuspend the pellets. Centrifuge briefly to drive the solution to the bottom of each bottle. Transfer the solution from all four bottles to two tared Oak Ridge tubes. Rinse each bottle with another 7.5 ml of TBS and add to the Oak Ridge tubes. Each tube should now have a total volume of 30 ml. Balance the tubes with TBS and mix the phage thoroughly by inversion.

7. Centrifuge the tubes at 10,100–22,700 g for 10 minutes at 4° C. to clear the supernatants. Transfer the supernatants to fresh, tared Oak Ridge tubes, and determine the volumes (1 g=1 ml).

8. Add 0.15 volume of PEG/NaCl solution to each tube, and invert gently approximately 100 times. Allow the phage to precipitate by incubating the tubes for at least 1 hour on ice. A heavy precipitate should appear.

9. Collect the precipitated phage by centrifuging at 10,100 g for 40 minutes at 4° C. Remove the supernatant as in Step 5 above.

10. Add 10 ml of TBS to each tube. Resuspend the phage pellet by gently vortexing, and then allowing the pellet to soften at room temperature for about 1 hour. Vortex again, and briefly centrifuge to drive the solution down. (If the phage are to be further purified on a CsCl density-gradient, add only 5 ml of TBS to each tube, resuspend the phage, and combine the two supernatants into a single Oak Ridge tube.)

11. Clear the supernatants by centrifuging the tubes at 10,100–22,700 g for 10 minutes at room temperature or 4° C. Pour the cleared supernatant from each tube into a 15-ml polypropylene snap-cap tube and store at 4° C. in the dark.

12. To determine the concentration and yield of phage particles, treat an aliquot of phage with 5×Lysis Mix (as in Step 2). Run 1- 5- and 10-µl samples on a 1.2% agarose gel in 4×GBB, using as a standard a known amount of phage treated in the same way. Include on the gel a sample from the original culture supernatant (Step 2) to calculate the percent yield. Electrophoretic analysis is also important for demonstrating that only one DNA species is present; this is especially important for fd-tet derivatives, which can delete the tetracycline genes, generating phage with approximately 6-kb genomes. The concentration of phage particles can be more accurately assessed by spectrophotometric analysis; however, this is better done with CSCl-purified phage. The infectious properties of the phage (TU/ml) can by analyzed by titering; the infectivity of fd-tet-derivatives is about 20 particles/TU, whereas that of wild-type derivatives is about 1 particle/pfu.

13. The final concentration of phage (if they are not to be CsCl-purified) should not exceed approximately $3 \times 10^{13}$/ml, so once the phage concentration is known, it should be adjusted accordingly with TBS. To impede cell growth, the solution can be adjusted to a final concentration of 0.02% (w/v) sodium azide or 20 mM $Na_2EDTA$. The phage can be stored long term in 50% (v/v) sterile glycerol at −18° C. (Barbas, F. et al., *Phage Display: A Laboratory Manual*, Cold Spring Harbor, N.Y. (2001)).

Phage Purification on CsCl Gradients

1. Following the large-scale preparation of phage above, the final volume of each preparation should be 10 ml.

2. Weigh out 4.83 g of CsCl into a tared 50-ml beaker. Tare the beaker again, and add the resuspended phage. Add TBS to a final weight of 10.75 g (over and above the weight of the vessel and CSCl: phage+TBS=10.75 g). This should give 12 ml of a 31% (w/w) solution of CsCl with a density of 1.3 g/ml. The density of the solution can be checked by weighing 1 ml in a tared beaker or plastic cup, and then returning it to the beaker it came from (be sure to first check that the pipet on that setting weighs 1 ml of water at 1 g). If necessary, adjust the density to 1.3 g/ml with CsCl or buffer.

3. Transfer the volume of each beaker into a polyallomer tube. Be sure that the tubes are filled to the top (as they can collapse during centrifugation), and if necessary, add extra volume with a 31% (w/w) solution of CsCl in TBS. Balance the tubes, by transferring solution from one to another, or by adding more CsCl solution to one tube. Place the tubes in a SW40 swinging-bucket rotor and centrifuge at 37,000 rpm for 48 hours at 5° C. For the 70.0 Ti rotor, spin at 58,000 rpm for 20 hours.

4. Carefully remove the tubes from the rotor, place in a rack, and set them up, one at a time, in a clamp stand. Illuminate the clamped tube from the top with a strong, visible light source (such as a halogen desk lamp). There will be two bands toward the top of the tube. The phage band, which will be faint, bluish, and homogeneous (smoky looking), should be just visible above a narrow, stringy, flocculent, opaque white band (which is probably PEG). In a good phage preparation, the phage band is about 5 mm in width, and its density is approximately 1.33 g/ml.

5. Attach a sterile pipet tip to an aspirator pump and adjust the aspirator to a moderate speed. Hold the pipet tip at the meniscus, and aspirate the fluid overlying the phage band to within 2 mm of the upper edge, being careful not to disturb the phage band. Withdraw the phage band with a polyethylene transfer pipet (preferably sterile), or, better yet, a sterile, glass transfer pipet attached to a peristaltic pump. The phage band will be viscous; try to avoid the flocculent band that lies underneath. If using a quickseal polyallomer tube, remove the band with syringe, as for CsCl-purified plasmid.

6. Transfer the extracted phage bands to a 26-ml, screw-cap polycarbonate centrifuge tube for the Beckman 60 Ti rotor. 4–6 phage bands can be pooled in a single bottle. Fill the tube to the shoulder with TBS, close the cap firmly, and invert repeatedly to mix. For centrifugation, balance against another tube filled with water.

7. Centrifuge the tubes in a Beckman 60 Ti fixed-angle rotor at 50,000 rpm for 4 hours at 4° C. to pellet the phage. Pour off and discard the supernatant, recentrifuge the pellet briefly at a low speed on a tabletop centrifuge, and discard the remaining supernatant, with the pellet pointed away from the liquid.

8. Resuspend the pellet in 10 ml of TBS; vortex gently, centrifuge briefly in a table-top centrifuge to drive the solution down, and allow the pellet to soften overnight at 4° C. Vortex to dissolve the pellet.

9. Top the bottle with TBS, recentrifuge to pellet the phage, and remove the supernatant as in Step 7. (Note: This step is optional, giving somewhat purer phage.)

10. Resuspend the pellet in TBS as in Step 9, using 12 ml of TBS per liter-equivalent of starting culture; this gives an anticipated concentration of $3 \times 10^{13}$ virions/ml. Transfer the phage to a sterile Oak Ridge tube and centrifuge at 6,500 g for 10 minutes.

11. Transfer the phage-containing supernatant to a 15-ml polypropylene, snap-cap tube. At this point, sodium azide can be added as a preservative to the cooled phage to a final concentration of 0.02% (w/v). Alternatively, $Na_2EDTA$ can be used at a final concentration of 20 mM.

12. Measure the concentration of phage particles spectrophotometrically, and/or by agarose gel electrophoresis.

13. Dilute the phage $10^{-7}$, $10^{-8}$ and $10^{-9}$ in TBS/gelatin and titer. Include the proper positive and negative controls A good infective titer (TU/ml) is approximately 5% of the concentration of physical particles (virions/ml).

14. Store the phage at 4° C. away from light, or in 50% glycerol at −18° C. for long-term storage. Under these conditions, titers are stable for at least several years. (Barbas, F. et al., *Phage Display: A Laboratory Manual*, Cold Spring Harbor, N.Y. (2001)).

(b) Preparation of Identical Phage Columns

Cross-Linking. Mix one volume of phage (all subsequent volumes in the paragraph are relative to this volume) at a concentration corresponding to 1.26 mM p VIII subunits in water with 0.15 volume 0.5 M NaCl and 0.15 volume 1 M $NaH_2PO_4$ (pH adjusted to 6.9 with NaOH). To this solution add 0.0026 volume of 76.3 mg/ml NHS-dextran. Immediately mix the reaction mixture by vortexing, add 0.15 volume 50% PEG, and vortex again. The phage will precipitate in the PEG solution (final concentration 5%). Rotate the reaction mixture for 12–16 hours in a sealed tube at room temperature, and quench unreacted N-hydroxy-succinamide by adding 8 volumes 1M ethanolamine (pH adjusted to 9 with HCl) and 0.89 volumes 5 M NaCl. Continue rotation for an additional 1–2 hours at room temperature. Dilute the cross-linked phage in TBS (at least 10 volumes) and wash 5–6 times by centrifugation, aspiration or decanting the supernatant, and resuspend the pellet in fresh TBS. Suspend the final pellet in 10 volumes TBS and store at 4° C.

Column Preparation. Pack two 0.5 ml columns (Amersham Pharmacia Biotech, HR 5/2, Code 18-0382-01), each with cross-linked phage equivalent to about $2 \times 10^{13}$ particles. Equilibrate the columns on an HPLC system with TBS (Other columns or non-column batch methods are also appropriate).

Sample Preparation. To dissociate bound proteins and other species, and to minimize protein interactions, make up aliquots (1.5 ml) of the original human CSF Samples 1 and 2 to a final concentration of 3M guanidine HCl and 0.2 M formic acid, and incubate in ice for 60 minutes. Then buffer exchange them using a HiTrap Desalting Column (Amersham Pharmacia Biotech) on an HPLC system at a flow rate of 5 ml/min with phosphate-buffered-saline (PBS) and collect in a final volume of 2 ml. Pass the low molecular weight flow-through over a SepPak column and wash with PBS to isolate peptides for additional analysis if desired. If the associations of proteins in the original sample are to be preserved, then omit the additions of guanidine HCl and formic acid, and dilute the CSF aliquots 1:2 with PBS before the next step.

(c) Capture Step Three (FIG. 5)

Sample Difference Proteins Captured By Phage Columns. Pass 1.5 ml of Samples 1 and 2 over a dedicated cross-linked phage column in TBS on an HPLC system at a flow rate of 20 μl/minute. Keep the flow-throughs, which are the depleted protein samples and which will be used in subsequent cycles. Wash the columns with 20 ml TBS at a flow rate of 0.5 ml/minute.

Figure 6:
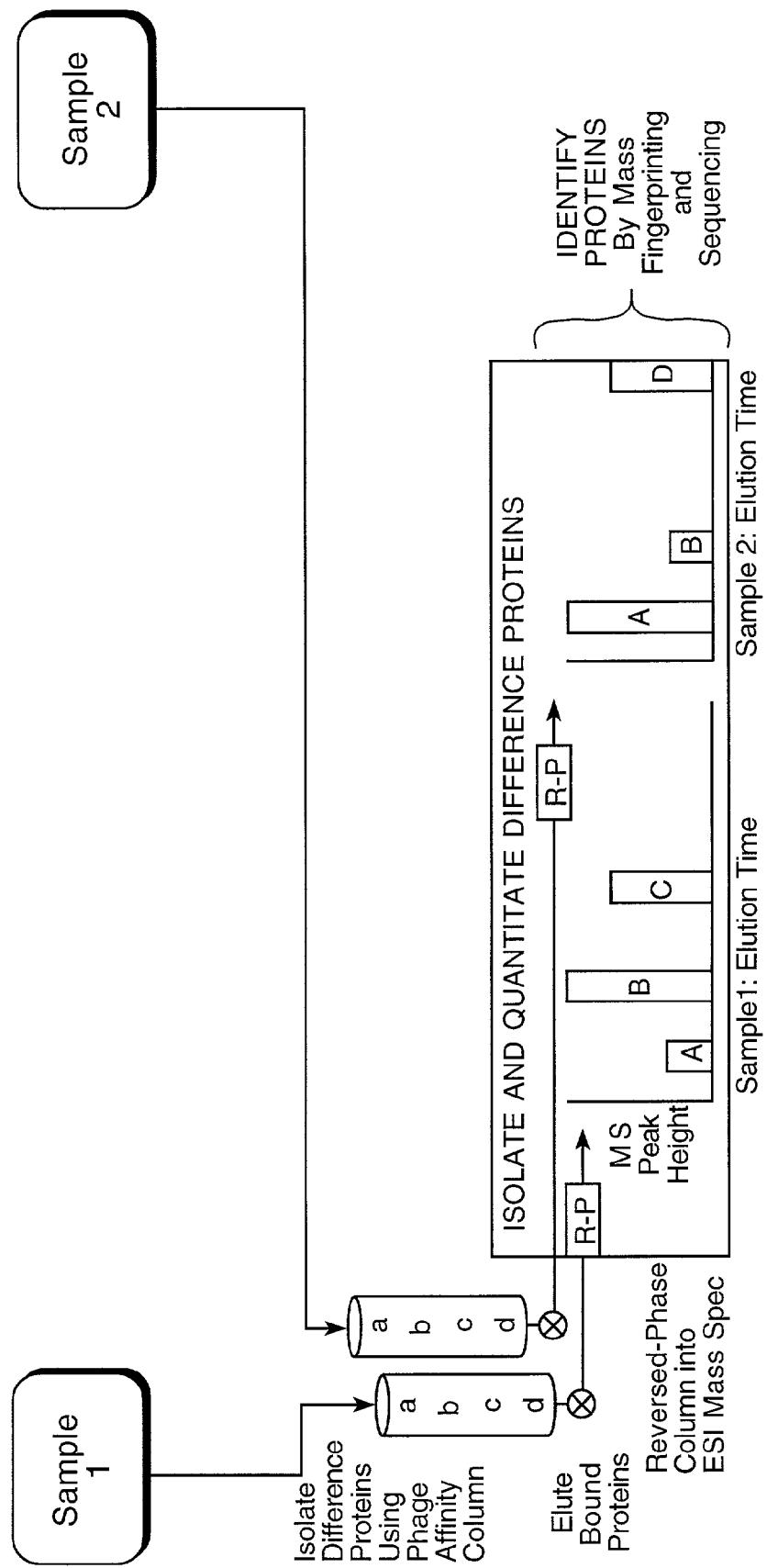
FIG. 6 is a schematic diagram showing the identification of proteins that differ between two separate complex biological samples by eluting proteins that bound to phage affinity columns and analyzing the proteins via mass spectrometry.

Step III: Quantitation and Identification of Difference Proteins (FIG. 6)

Isolate Difference Proteins Using Phage Affinity Columns. Elute the bound proteins from the columns with 1 ml Panning Elution Buffer (0.1 M HCl adjusted to pH 2.2 with glycine) at a flow rate of 0.5 ml/minute and collect 100 μl fractions. Pool the fractions and neutralize with about 140 μl 1M Tris Base, pH 9.1. Verify the pH has been raised to yield a solution of pH 7.0–8.2.

(a) Analysis by Cation Exchange/Reversed-Phase Columns and Electrospray Mass Spectrometry Digestion of proteins to Peptides. Lyophilize the samples prepared above, and resolubilize in 8 M urea, 200 mM $NH_4HCO_3$, and 20 mM $CaCl_2$ and quantify using a Bradford assay. Add Endoprotease Lys-C (Boehringer-Mannheim) to a final substrate-to-enzyme ratio of 100:1, and incubate at 37° C. for 15 hours. Dilute the Lys-C digestion fourfold with water, and add modified trypsin (Boehringer-Mannheim) to a final substrate-to-enzyme ratio of 50:1. Incubate the trypsin digestion mixture at 37° C. for 15 hours. Desalt the peptide mixture on a reversed-phase column, lyophilize, and resuspend in 5 mM $K_2HPO_4$, 5% acetonitrile (pH3) (other chemical and enzymatic digestion methods are also appropriate).

(b) 2D Chromatographic Separation of Peptides.

Biphasic Microcapillary Column. Construct the biphasic column, by pulling a fused-silica capillary (100 μm i.d.×365 μm o.d.) with a $CO_2$-based laser puller to make a fritless column. Pack the column first with 8 cm of 5 μm C18 RP particles (218TP C18 Vydac) and then with 4 cm of 5 μm strong cation exchange particles (PolySULFOETHYL Aspartamide; Poly LC).

Peptide Separation. Load the peptide mixtures onto the biphasic microcapillary column. Displace peptide fractions from the SCX to the RP particles using the following salt step gradients: (1) 0% (1') 0% (1"), 0% (1''') 0% (2) 0–10% (3) 10–20% (4) 20–30% (5) 30–40% (6) 40–100% of SCX-b', and (7) 100% SCX-C'. Elute peptides from the RP particles into the mass spectrometer using a linear gradient of 0–60% RP-B over 30 minutes at 300 nl/minute. Mobile-phase buffers are, for RP-A buffer, 0.5% acetic acid, 5% acetonitrile; for RP-B, 0.5% acetic acid, 80% acetonitrile; for SCX-B', 0.5% acetic acid, 5% acetonitrile, 250 mM KCl; for SCX-C', 0.5% acetic acid, 5% acetonitrile, 500 mM KCl (other spearation methods are also appropriate).

Mass Spectrometric Analysis. Perform mass spectrometric analysis on a Finnigan LCQ ion trap mass spectrometer (Finnigan Corp., San Jose, Calif.) run and operate as described. Directly couple an Integral chromatography workstation (PE Biosystems, Foster City, Calif.) to an LCQ ion trap mass spectrometer equipped with an electrospray ion source. Operate the electrospray needle with a voltage differential of 5.5 kV, and hold the heated desolvation capillary at 250° C.

Identify and Quantitate Via Mass Fingerprinting and Sequencing With Electrospray Mass Spectrometry. For automated spectrum and data analysis, process each raw tandem spectrum as described here. First identify spectra derived from single or multiply charged parent ions. Correlate processed tandem mass spectra with standard ORFs using the program SEQUEST running on a DEC Alpha workstation. Perform all searches without considering the protease used because many proteins in the mixtures do not digest to completion. For multiply charged peptides, use the following criteria to determine whether to select the +2 or +3 charge state: (1) Choose a particular charge state if the cross-correlation score is greater than or equal to 1 U more than that of the other charge state. (2) Assign a score to each charge state (+5 for tryptic start, +5 for tryptic end, +2 if the cross-correlation score is greater than the other charge state, +2 if the preliminary score ranking is less than 50, and the charge state with the highest score is chosen. Use the selected charge of the peptide in the final protein identification analysis and the SEQUEST output from the other charge state discarded. Filter the correlation results using the value of the cross-correlation score and the matched sequence for each spectrum. For singly charged peptides, retain spectra with a cross-correlation score to a tryptic peptide great than or equal to 1.5. For multiply charged peptides, retain spectra with a cross-correlation to a tryptic peptide greater than or equal to 2. Eliminate all spectra with cross-correlation scores not meeting these criteria from further consideration. For the protein identifications, sort the filtered results to show unique peptide sequences that are derived from the same annnotated ORFs in the genome. Protein identifications based on mass spectra correlating to one or more unique tryptic peptides are considered valid identifications. Single peptides that alone identify a protein are manually validated after meeting the following criteria. First, the SEQUEST cross-correlation score must be greater than 1.5 for a +1 tryptic peptide or greater than 2 for a +2 or +3 tryptic peptide. Second, the MS/MS spectrum must be of good quality with fragment ions clearly above baseline noise. Third, there must be some continuity to the b or y ion series. Fourth, the y ions that correspond to a proline residue should be intense ions. Fifth, unidentified, intense fragment ions either correspond to +2 fragment ions or the loss of one or two amino acids from one of the ends of the peptide. After going through this process one can be fairly confident of a protein identification. For proteins common to Samples 1 and 2, approximate relative abundance ratios can be determined using Finnigan LCQUAN software and peak heights of molecular ions (Link, A. J., et al., Direct Analysis of Protein Complexes Using Mass Spectrometry. *Nature Biotechnology* 17:676–682 (1999)).

Step IV: Isolation of Affinity Reagents Against Difference Proteins

Figure 7:
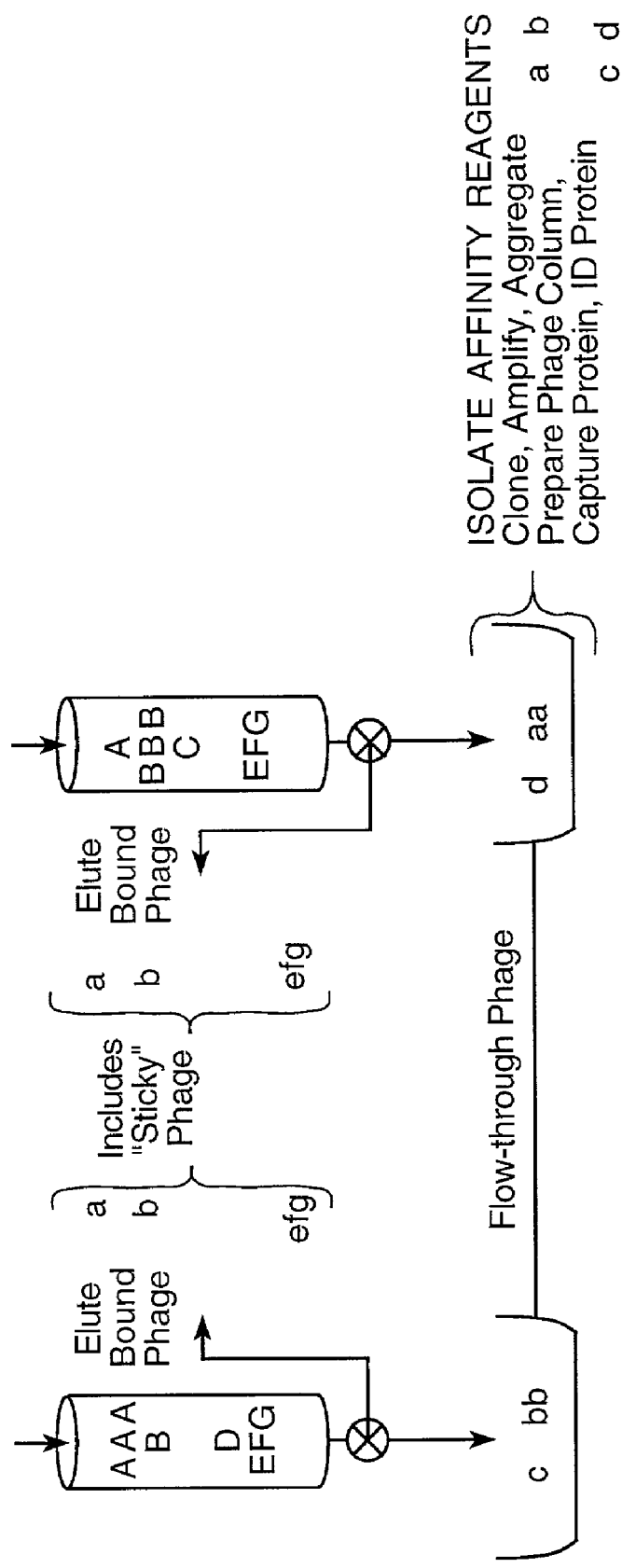
FIG. 7 is a schematic diagram showing the isolation of affinity reagents against proteins that differ between two complex biological samples.

Pool the flow-through phage as indicated in FIG. 7. Amplify phage, prepare phage affinity matrices and phage columns, and capture difference proteins as described in steps II(a)–(c) above. The number of proteins identified in step III (i.e. the step involving the quantitation and identification of difference proteins) (FIG. 6) is a guide to the numbers of distinct phage clones that need to be tested.

Assignment of phage clone specificity to identified protein is carried out as follows:

1. Isolate Captured Protein Using Phage Affinity Columns. Elute the bound protein from the column with 1 ml Panning Elution Buffer (0.1 M HCl adjusted to pH 2.2 with glycine) at a flow rate of 0.5 ml/minute and collect 100 µl fractions. Pool the fractions and neutralize with about 140 µl 1 M Tris Base, pH 9.1. Verify the pH has been raised to yield a solution of pH 7.0–8.2.

2. Identify Eluted Protein. The eluted protein is identified using an LCQ Mass Spectrometer as described in step III above, and illustrated in FIG. 6, except that since the major component should be a single protein, the sample can be directly sprayed into the instrument.

3. Assign Phage Clone to Identified Protein. The association of a particular phage clone with the identity of the protein it captures, allows its specificity to be defined. The phage provide a specific affinity reagent against the protein, and if necessary, the identity of the peptide or antibody can be determined to allow the production of high purity peptide or antibody, via well established methods. Multiple distinct phage clones may be isolated which bind to the same protein. Their affinities may determine their utility.

Step V: Depletion of Most Abundant Proteins (FIG. 8)

Prepare protein affinity matrices and perform initial capture step as described in steps I(a) and (b) above. Elute the bound phage as indicated in FIG. 2 with 1 ml Panning Elution Buffer (0.1 M HCl adjusted to pH 2.2 with glycine) at a flow rate of 0.5 ml/minute and collect fractions. Pool the fractions containing phage, buffer exchange using a HiTrap Desalting Column (Amersham Pharmacia Biotech) on an HPLC system at a flow rate of 5 ml/min with TBS, and collect in a final volume of about 1 ml.

Figure 9:
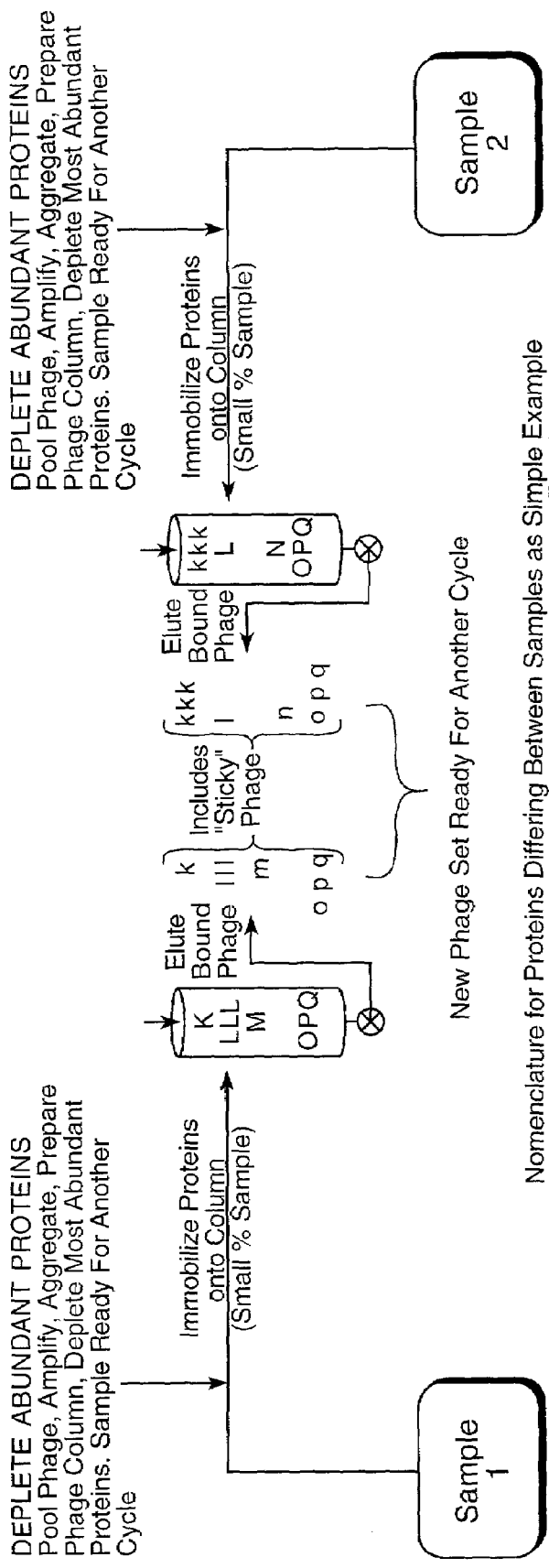
FIG. 9 is a schematic diagram showing the capture of less abundant proteins following the depletion of abundant proteins from a pair of complex biological samples.

Most Abundant Proteins Captured By Phage Columns. Pool the eluted phage from Columns 1 and 2. Amplify phage, prepare phage affinity matrices and phage columns, and capture difference proteins using the procedures described in steps II(a)–(c) above. Pass 1.5 ml of Samples 1 and 2 over a dedicated cross-linked phage column in TBS on an HPLC system at a flow rate of 20 µl/minute. Keep the flow-throughs, which are the depleted protein samples and which will be used for the next cycle (FIG. 9). Wash the columns with 20 ml TBS at a flow rate of 0.5 ml/minute.

Isolate Difference Proteins Using Phage Affinity Columns. Elute the bound proteins from the columns with 1 ml Panning Elution Buffer (0.1 M HCl adjusted to pH 2.2 with glycine) at a flow rate of 0.5 ml/minute and collect 100 µl fractions. Pool the fractions and neutralize with about 140 µl 1M Tris Base, pH 9.1. Verify the pH has been raised to yield a solution of pH 7.0–8.2. The eluted proteins can be further purified if necessary, and can be an invaluable source of "native" material for further structural and functional studies, including providing a standard for the development of immunoaffinity based assays using the specific affinity reagents isolated from DPCP.

Step VI. New Cycle with Less Abundant Proteins

Using the flow-throughs from Step V, which are the depleted protein samples, the cycle described above is repeated (FIG. 9).

Step VII. Continuing Depletion of Abundant Proteins

Steps V and VI can be continuously repeated until the limits of detection of the analytical device have been reached.

OTHER EMBODIMENTS

Although the present invention has been described with reference to preferred embodiments, one skilled in the art can easily ascertain its essential characteristics and without departing from the spirit and scope thereof, can make various changes and modifications of the invention to adapt it to various usages and conditions. Those skilled in the art will recognize or be able to ascertain using no more than routine experimentation, many equivalents to the specific embodiments of the invention described herein. Such equivalents are intended to be encompassed in the scope of the present invention.

All publications and patents mentioned in this specification are herein incorporated by reference.

What is claimed is:

1. A method of identifying differences in expression of polypeptides between two samples, said method comprising:
   (a) providing one or more first arrays comprising one or more polypeptides from a first complex biological sample adhered to a first type of support;
   (b) providing one or more second arrays comprising one or more polypeptides from a second complex biological sample adhered to a second type of support;
   (c) exposing a peptide-nucleic acid coupled library comprising a plurality of members (i) to one of said first arrays at least one time to create a first product, said first product comprising one or more members of said peptid-nucleic acid coupled library that reversibly bind to said first array and (ii) to one of said second arrays at least one time to create a third product, said third product comprising one or more members of said peptide-nucleic acid coupled library that reversibly bind to said second array;
   (d) exposing said first product to one of said second arrays at least one time to create a second product, said second product comprising one or more members of said first product that do not bind to said second array and;
   (e) exposing said third product to one of said first arrays at least one time to create a fourth product, said fourth product comprising one or more members of said third product that do not bind to said first array,
   wherein a member of said peptide-nucleic acid coupled library in said second product binds to a polypeptide in said first biological complex sample that is expressed in a greater amount than in said second complex biological sample and a member of said peptide-nucleic acid coupled library in said fourth product binds to a polypeptide in said second biological sample that is expressed in a greater amount than in said first biological sample.

2. The method of claim 1, further comprising the step of:
   (f) comparing said second product and said fourth product.

3. The method of claim 1, further comprising the steps of:
   (f) combining said second and fourth products to produce a pooled product; and
   (g) amplifying said pooled product.

4. The method of claim 3, further comprising the steps of:
   (h) providing one or more third arrays comprising one or more members from said amplified pooled product adhered to a third support; and
   (i) exposing said first or second complex biological sample to one of said third arrays at least one time to provide a fifth product, said fifth product comprising one or more polypeptides from said first or second complex biological sample that reversibly bind to said third array.

5. The method of claim 4, further comprising the step of:
   (j) exposing said first or second complex biological sample to one of said third arrays at least one time to provide a sixth product, said sixth product comprising one or more polypeptides from said first or second complex biological sample that reversibly bind to said third array, wherein said complex biological sample is different from that used in step (i).

6. The method of claim 5, further comprising the step of:
   (k) comparing said fifth product and said sixth product.

7. The method of claim 1, wherein said first or second complex biological sample is from a tissue.

8. The method of claim 7, wherein said tissue is selected from the group consisting of epithelial, connective, muscle, and nerve.

9. The method of claim 1, wherein said first or second complex biological sample is from a body fluid.

10. The method of claim 9, wherein said body fluid is selected from the group consisting of cerebrospinal fluid, blood, saliva, mucous, tears, pancreatic juice, seminal fluid, sweat, milk, bile, plasma, serum, lymph, urine, pleural effusions, bronchial lavage, ascities, and synovial fluid.

11. The method of claim 10, wherein said body fluid is cerebrospinal fluid.

12. The method of claim 1, wherein said first or second complex biological sample is from an organ or tissue.

13. The method of claim 12, wherein said organ or tissue is selected from the group consisting of skin, bone, cartilage, tendon, ligament, skeletal muscle, smooth muscle, heart, blood, blood vessel, brain, spinal cord, peripheral nerve, nose, trachea, lung, mouth, esophagus, stomach, intestine, kidney, uterus, ureters, urethra, bladder, hypothalamus, pituitary, thyroid, pancreas, adrenal gland, ovary, oviduct, vagina, mammary gland, testicle, seminal vesicle, penis, lymph, lymph node, lymph vessel, white blood cell, T-cell and B-cell.

14. The method of claim 1, wherein said first or second complex biological sample is from a cultured cell.

15. The method of claim 14, wherein said cell is derived from epithelial, connective, muscle or nervous tissue.

16. The method of claim 1, wherein one of the complex biological samples is from a diseased individual and the other complex biological sample is from a non-diseased individual.

17. The method of claim 1, wherein one of the complex biological samples is from a medicated individual and the other complex biological sample is from a non-medicated individual.

18. The method of claim 1, wherein said library is a phage display library.

19. The method of claim 18, wherein said library is an antibody library.

20. The method of claim 18, wherein said library is a recombinant display library.

21. The method of claim 18, wherein said library is a synthetic peptide library.

22. The method of claim 1, further comprising treating the first or second complex biological sample prior to adhering said one or more polypeptides to said support.

23. The method of claim 22, wherein said treating comprises denaturing said one or more polypeptides.

24. The method of claim 1, wherein the support of step (a) or step (b) is a solid support.

25. The method of claim 1, wherein both the support of step (a) and the support of step (b) are solid supports.

26. The method of claim 1, wherein said one or more polypeptides from said first or second complex biological samples are crosslinked to said support.

27. The method of claim 1, wherein said one or more polypeptides from said first and second complex biological samples are crosslinked to said support.

28. The method of claim 4, wherein said fifth product comprises one or more polypeptides from said first or second complex biological sample that bound to the third array during the exposing step (i) and were subsequently released.

29. The method of claim 5, wherein said sixth product comprises one or more polypeptides from said first or second complex biological sample that bound to the third array during the exposing step (j) and were subsequently released.

30. The method of claim 1, further comprising the step of amplifying said second product.

31. The method of claim 1, further comprising the step of amplifying said fourth product.

32. The method of claim 1, further comprising analyzing said second product via mass spectrometry.

33. The method of claim 1, further comprising analyzing said fourth product via mass spectrometry.

34. The method of claim 4, further comprising analyzing said fifth product via mass spectrometry.

35. The method of claim 5, further comprising analyzing said sixth product via mass spectrometry.

36. The method of claim 6, wherein said fifth and sixth products are compared using mass spectrometry.

37. The method of claim 1, wherein said library is exposed to the first array more than one time to create said first product.

38. The method of claim 1, wherein said first product is exposed to the second array more than one time to create said second product.

39. The method of claim 1, wherein said library is exposed to the second array more than one time to create said third product.

40. The method of claim 1, wherein said third product is exposed to the first array more than one time to create said fourth product.

41. The method of claim 4, wherein the first or second complex biological sample of step (i) is exposed to the third array more than one time to create said fifth product.

42. The method of claim 5, wherein the first or second complex biological sample of step (j) is exposed to the third array more than one time to create said sixth product.

43. The method of claim 1, wherein the first arrays of step (c) and step (e) are the same array.

44. The method of claim 1, wherein the first arrays of step (c) and step (e) are separate arrays.

45. The method of claim 1, wherein the second arrays of step (d) and step (c) are the same array.

46. The method of claim 1, wherein the second arrays of step (d) and step (c) are separate arrays.

47. The method of claim 5, wherein the third arrays of step (j) and step (i) are the same array.

48. The method of claim 5, wherein the third arrays of step (j) and step (i) are different arrays.

49. The method of claim 1, wherein said first and second complex biological samples are from different subjects.

* * * * *